United States Patent [19]
Wholey

[11] Patent Number: 5,383,897
[45] Date of Patent: Jan. 24, 1995

[54] METHOD AND APPARATUS FOR CLOSING BLOOD VESSEL PUNCTURES

[75] Inventor: Mark H. Wholey, Oakmont, Pa.
[73] Assignee: Shadyside Hospital, Pittsburgh, Pa.
[21] Appl. No.: 165,061
[22] Filed: Dec. 10, 1993

Related U.S. Application Data
[63] Continuation of Ser. No. 962,816, Oct. 19, 1992, abandoned.

[51] Int. Cl.$^6$ ............................................. A61B 17/00
[52] U.S. Cl. .................................................. 606/213
[58] Field of Search ............... 606/139, 151, 157, 158, 606/213

[56] References Cited

U.S. PATENT DOCUMENTS

| | | |
|---|---|---|
| 3,221,746 | 12/1965 | Noble . |
| 3,266,113 | 8/1966 | Flanagan, Jr. . |
| 3,276,448 | 10/1966 | Kronenthal ........................ 606/151 |
| 3,874,388 | 4/1975 | King et al. ......................... 606/213 |
| 3,981,051 | 9/1976 | Brumlik . |
| 4,169,303 | 10/1979 | Lemelson . |
| 4,214,587 | 7/1980 | Sakura, Jr. . |
| 4,259,959 | 4/1981 | Walker .............................. 606/213 |
| 4,593,693 | 6/1986 | Schenck . |
| 4,617,932 | 10/1986 | Kornberg . |
| 4,665,917 | 5/1987 | Clanton et al. . |
| 4,744,364 | 5/1988 | Kensey .............................. 606/213 |
| 4,917,087 | 4/1990 | Walsh et al. ....................... 606/153 |
| 4,920,235 | 4/1990 | Yamaguchi ........................ 174/36 |
| 4,997,439 | 3/1991 | Chen ................................... 606/216 |
| 5,047,047 | 9/1991 | Yoon .................................. 606/216 |
| 5,171,253 | 12/1992 | Klieman ............................. 606/157 |
| 5,234,448 | 8/1993 | Wholey et al. .................... 606/155 |
| 5,254,127 | 10/1993 | Wholey et al. .................... 606/153 |

OTHER PUBLICATIONS

H. Han et al., "A mechanical surface adhesive using micromachined silicon structures", *J. Micromech. Microeng.* 1 (1991), pp. 30-33.

Hongtao Han et al., "Mating and Piercing Micromechanical Structures for Surface Bonding Applications", a paper presented at the Microelectro Mechanical Systems Workshop in Jan., 1991, in Nara, Japan.

"A Stitch in time with 'Velcro' chips" *New Scientist*, Apr. 6, 1991.

"The World's Greatest Invention Goes Micro", *Briefings*, Mar. 22, 1991.

"Sticking with Silicon micromushrooms" *Science*, Mar. 2, 1991.

*Primary Examiner*—Tamara L. Graysay
*Attorney, Agent, or Firm*—Buchanan Ingersoll; Lynn J. Alstadt

[57] ABSTRACT

A closure for sealing punctures in blood vessels utilizes a sheet adapted to conform to the inner surface of a blood vessel which sheet has a plurality of barbs attached to one surface. A pusher rod connects to the barbed surface. The sheet is pushed through a sheath that has been inserted into the puncture until the sheet is within the blood vessel. Then, the pusher rod pulls the sheet against the blood vessel inner wall to anchor it over the puncture. The pusher rod is then released from the sheet and both the sheath and pusher rod are removed completing the closure.

13 Claims, 4 Drawing Sheets

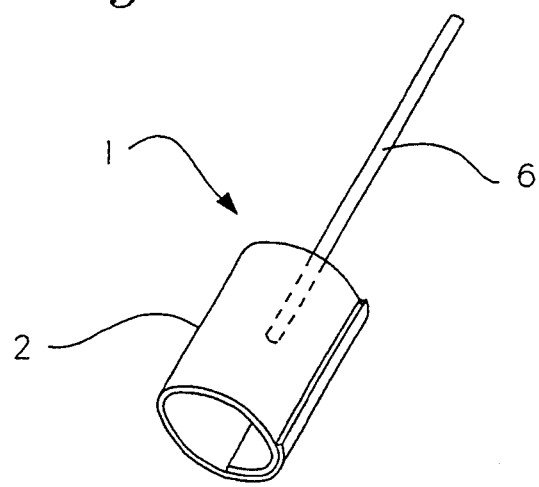
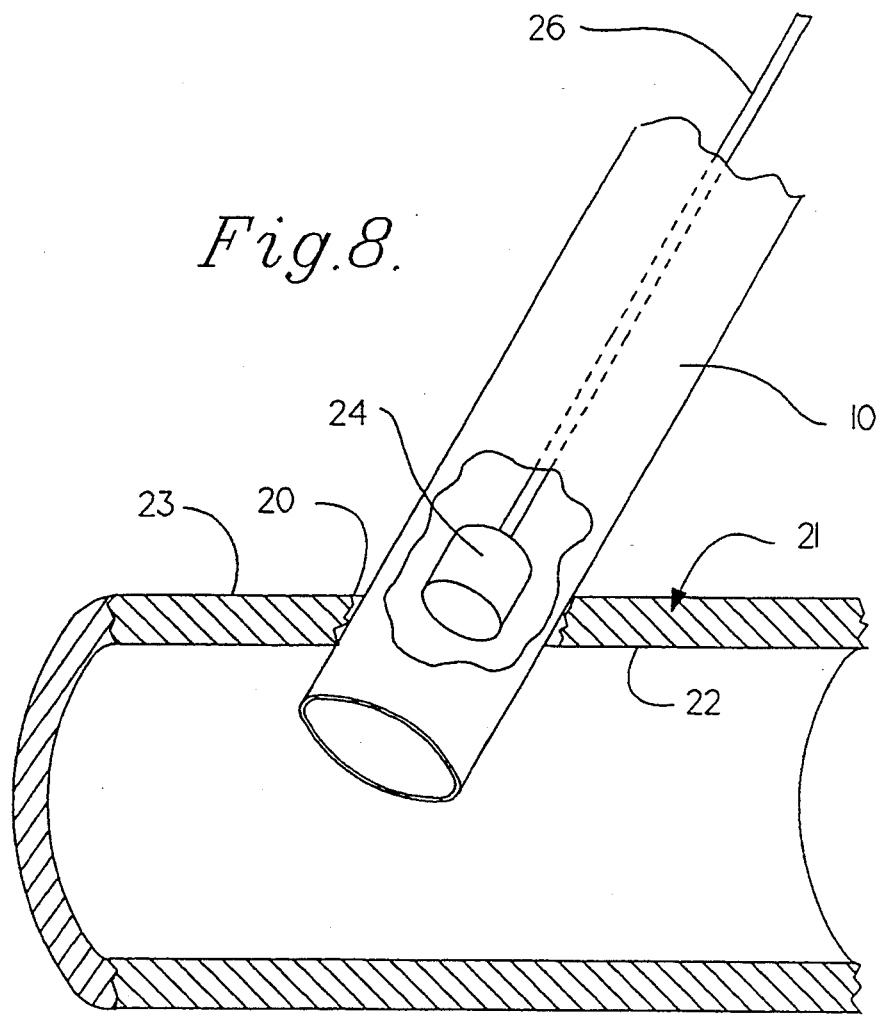

METHOD AND APPARATUS FOR CLOSING BLOOD VESSEL PUNCTURES

This application is a continuation of application Ser. No. 07/962,816, filed Oct. 19, 1992, now abandoned.

BACKGROUND OF THE INVENTION

1. Field of Invention

The invention relates to a method and apparatus for closing a hole or puncture which has been made in a blood vessel.

2. Description of the Related Art

In several surgical procedures it is necessary to puncture a blood vessel in order to insert a tube into the blood vessel. Typically, the tube is a sheath in the 8–11 French size, and, consequently the hole following sheath removal, can be quite significant. Frequently, after conventional diagnostic arteriography, whether for the peripheral circulation or for the coronary circulation, excessive bleeding occurs on removal of the catheter or femoral artery sheath. Furthermore, the hematomas can be more significant, and the bleeding complications greater, in those post-interventional procedures in both cardiology and radiology. People who have hypertension, obesity, bleeding disorders or post thrombolitic therapy and people under medications which inhibit clotting, are all high risk patients for excessive bleeding to occur following removal of the sheath. The present medical practice is to first attempt to close the puncture by use of mechanical compression or a collagen plug. If these techniques do not promptly cause a clot to form closing the puncture, significant blood loss can occur. In these instances, microvascular surgery may be an option.

The refinements of technique in microvascular surgery have developed in two directions. The first approach is the use of microsuture techniques. These surgical techniques have advanced with the aid of the development of operating microscopes, microsutures and miscroinstruments. They produce very accurate anastomosis and yield good results. However, the techniques have not been widely used because they not only have the disadvantage of being time consuming, but they also have the disadvantage of requiring an extremely high degree of technical skill. The presence of suture material in the interior of a blood vessel can also present a nidus for clot formation.

The second approach has been in the direction of various mechanical devices or glues which attempt to circumvent the exacting skill and prolonged time required for the suturing techniques. The glues have generally been unsuccessful because of complications involving tissue toxicity and reaction. Stapling techniques have been cumbersome and have been difficult to use on vessels under 2 mm. in size. Other devices have included various tubes, flanges and rings. These devices are not suitable for rapid placement over a puncture. Moreover, excessive bleeding can still occur. Therefore, there is a need for a method and apparatus for closing blood vessel punctures which is particularly useful for those patients who are at high risk of bleeding from such punctures. Preferably the closure should be capable of placement over the puncture by insertion through the sheath for which the puncture was made.

In my U.S. Pat. application Ser. No. 07/843,384, now U.S. Pat. No. 5,234,448, I disclose a stent for sealing severed blood vessels. That stent includes a flexible sheet having micromechanical barbs which wraps around the outer surface or inner surface of the severed blood vessel. Although this closure can be wrapped around a blood vessel to cover a puncture, significant blood loss could occur while that closure is being fitted in place. Furthermore, this type of closure encircles the entire blood vessel rather than covering only the puncture site and adjacent area necessary to accomplish closure.

It would be preferable for the closure to be placed over the puncture prior to or immediately after removal of the sheath thereby minimizing blood loss through the puncture.

SUMMARY OF THE INVENTION

I provide a closure for puncture sites which is placed over the puncture on either the inside or the outside of the blood vessel. The closure is preferably delivered to the puncture through the sheath for which the puncture typically has been made. This closure is comprised of a flexible sheet having micromechanical barbs on one surface. A pusher rod is connected to the sheet. This should be a pivotable connection capable of being released. The flexible sheet is either pivoted to be in line with the pusher rod or wrapped around the pusher rod. In that orientation, the device is inserted through the sheath to a position within or above the blood vessel. Then the closure is oriented so that the barbed surface can be moved into contact with the blood vessel wall. The pusher rod is then used to pull or push the flexible sheath against the inside surface or outside surface of the blood vessel wall to cover the puncture. The barbs extending from the sheet anchor into the blood vessel wall and retain the closure over the puncture. The pusher rod then releases from the closure sheet to complete the procedure.

Other objects and advantages of my closure and method of using same will become apparent from a description of the present preferred embodiments thereof shown in the drawings.

BRIEF DESCRIPTION OF THE INVENTION

FIG. 7 is a perspective view showing the embodiment of FIG. 1 with the flexible sheet rolled about the pusher rod.

FIG. 8 is a perspective view similar to FIGS. 2 and 3 wherein an ultrasonic transducer has been inserted into the sheath prior to insertion of the closure.

DESCRIPTION OF THE PREFERRED EMBODIMENTS

Figure 1:
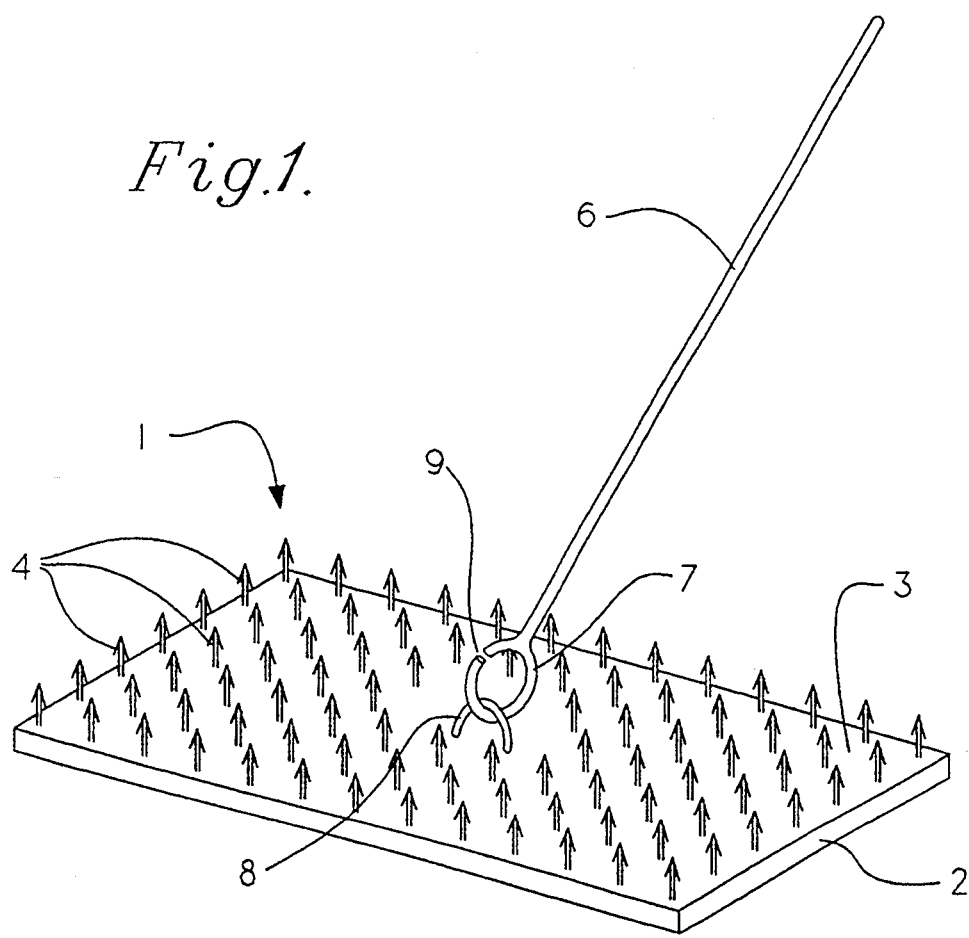
FIG. 1 is a perspective view of a present preferred embodiment of my closure.
Figure 4:
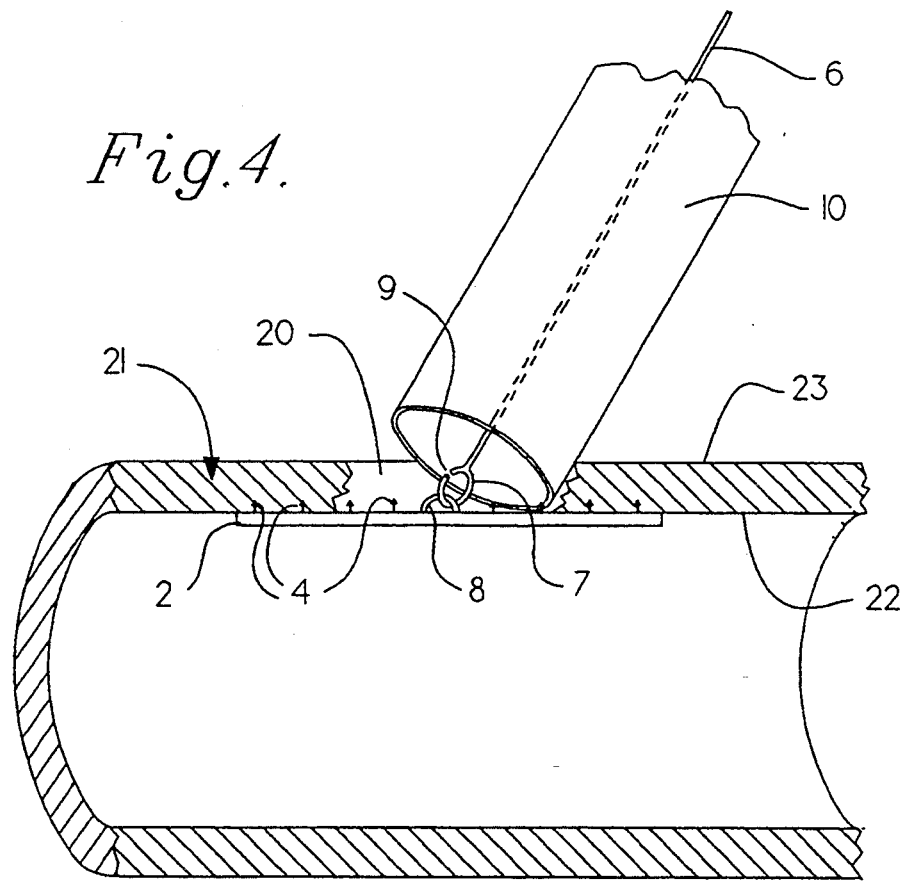
FIG. 4 is a view similar to FIGS. 2 and 3 showing the closure in place and the sheath and pusher rod being removed.
Figure 6:
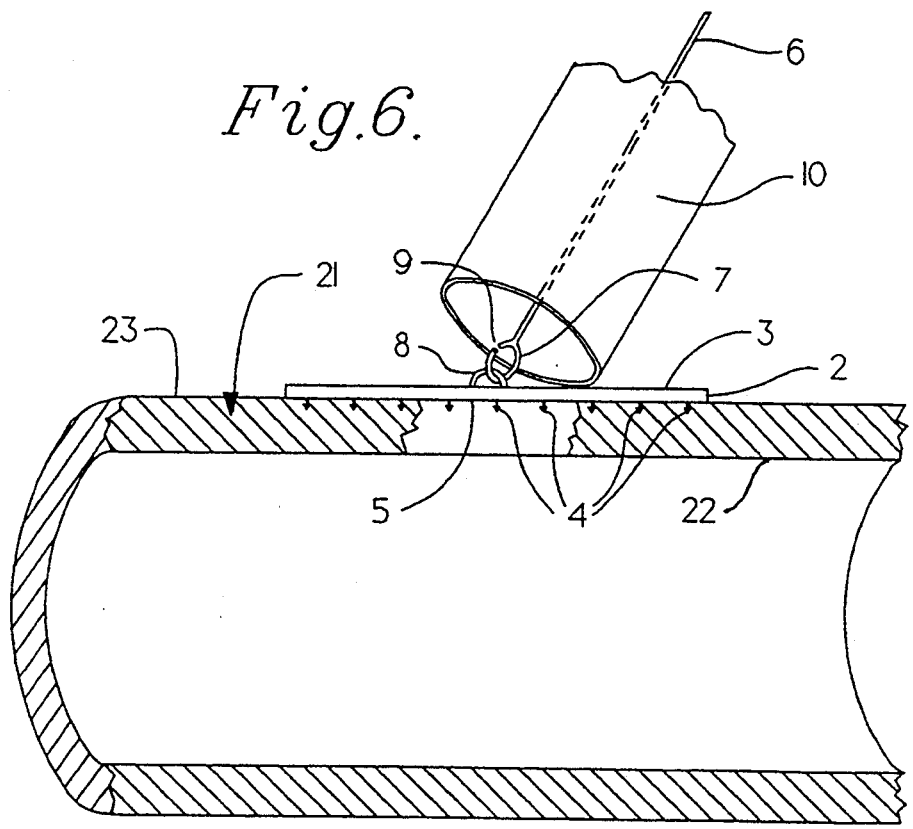
FIG. 6 is a perspective view similar to FIG. 5 showing the closure in place on the exterior of the blood vessel.

As shown in FIG. 1, my patch or closure 1 is comprised of a flexible sheet 2 having a plurality of barbs 4 extending from the top surface 3. The barbs 4 cover and are distributed throughout the top surface 3 as shown in the drawing. Consequently, when the closure 2 is placed over an opening as shown in FIGS. 4 and 6, several barbs 3 will penetrate the wall of the blood vessel. The barbs 3 are sized so as not to pass through the wall of the blood vessel, but to become embedded therein. A number of barbs are provided to assure that the closure will remain in place. A multiplicity of barbs, at least more than 6 barbs must penetrate the blood vessel wall to assure that the closure will not dislodge. A connector 8 is provided at the center of the flexible sheet 2, pusher rod 6 is attached to connector 8 using loop 7. That loop may be designed to open and close to release the sheet. Alternatively, it may have a slot 9 through which the pusher rod can be disengaged from the connector. Similarly, connector 8 may have a slot (not shown) through which the pusher rod can be released.

Figure 2:
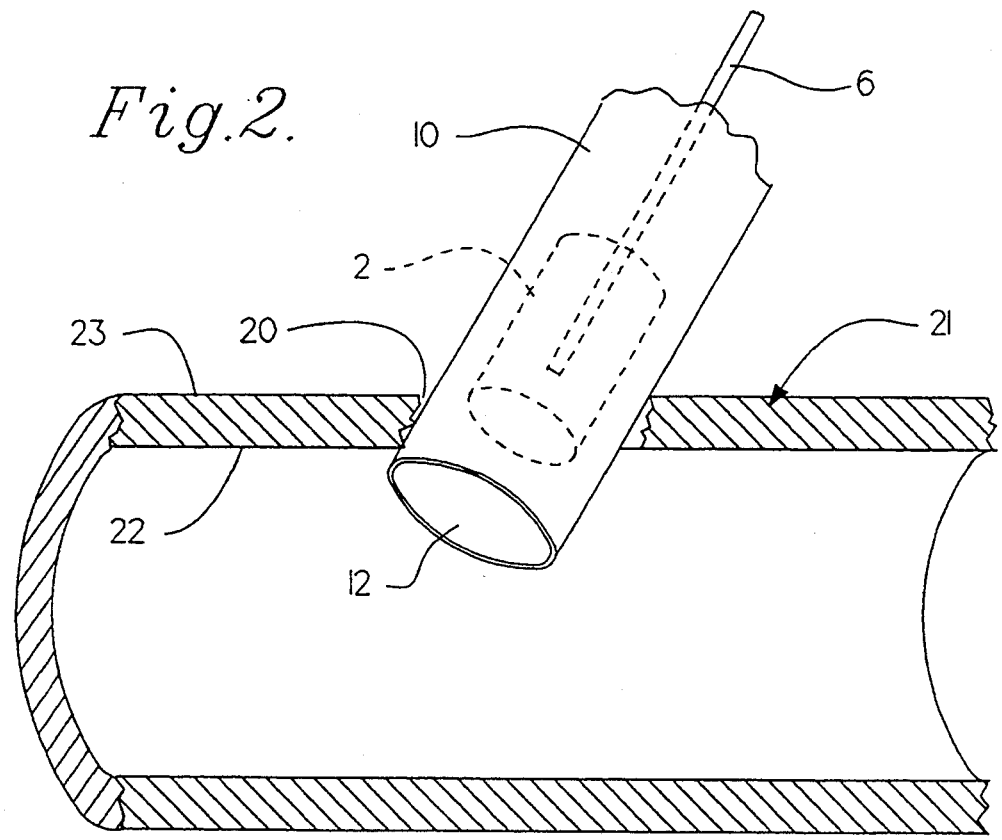
FIG. 2 is a perspective view partially in section showing a sheath inserted into a blood vessel wherein the closure is being advanced through the sheath.
Figure 3:
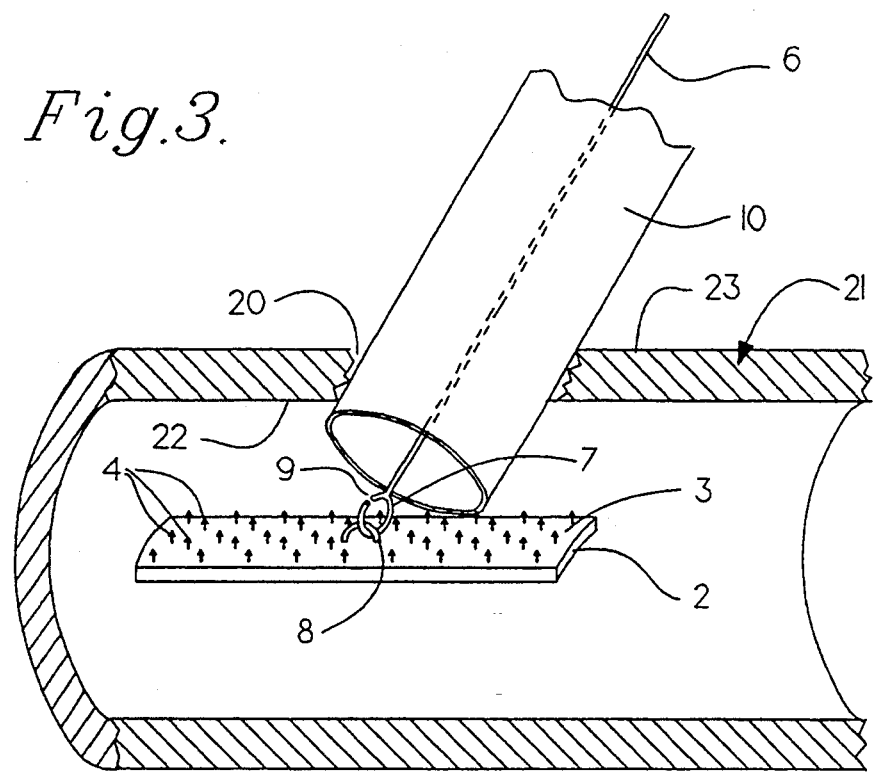
FIG. 3 is a view similar to FIG. 1 showing a closure within the blood vessel and being pulled into place.

Referring now to FIGS. 2 thru 4, there is shown a blood vessel 21 having a puncture 20 through which sheath 10 has been inserted. My closure 1 is inserted into the sheath as shown in FIG. 2. The closure sheet 2 is pivoted with respect to pusher rod 6 to enable both the sheet 2 and the pusher rod 6 to pass through the sheath 10. The flexible sheet is pushed into the blood vessel as shown in FIG. 3. At that point both the sheet 2 and pusher rod 6 are retracted so that sheet 2 is seated against the puncture as shown in FIG. 4. The barbs 4 provided on the top surface of the closure will penetrate the interior 22 of the blood vessel wall and anchor the closure sheet 2 over the puncture. To complete the procedure the pusher rod 6 is disengaged from the closure sheet 2 and both the sheath 10 and pusher rod 6 are removed.

Figure 5:
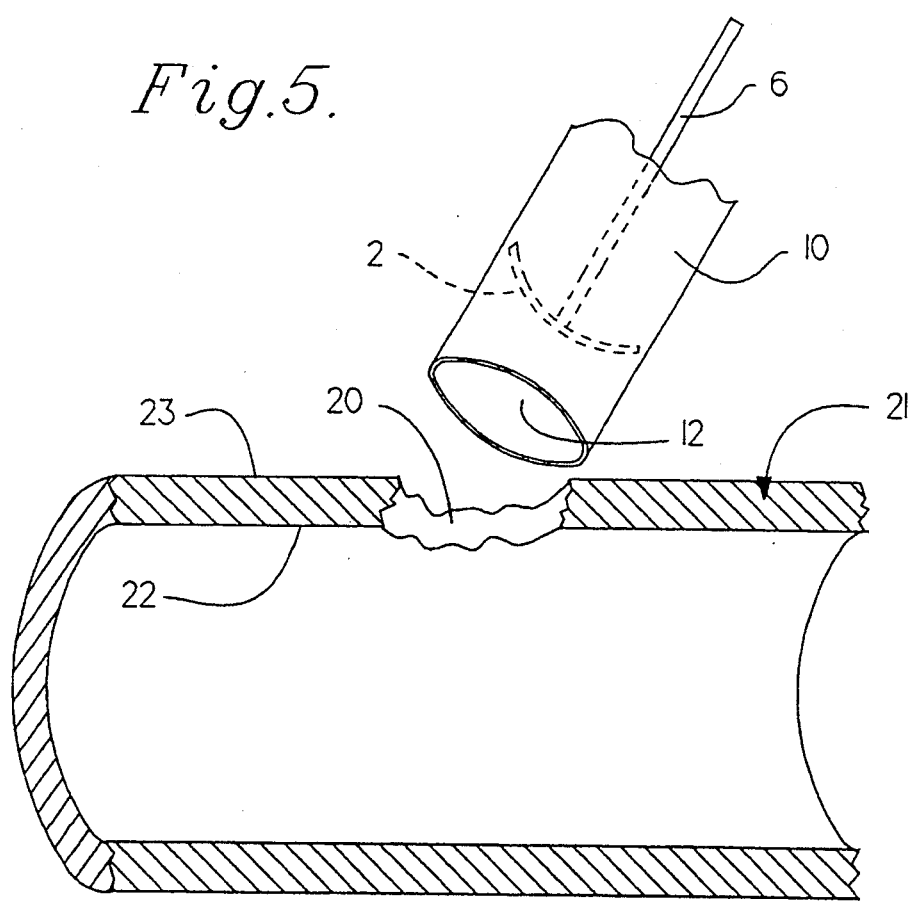
FIG. 5 is a perspective view partially in section showing the sheath removed and the closure positioned within the sheath for placement in the exterior of the blood vessel.

As shown in FIGS. 5 and 6, the sheath 10 which had been placed in the blood vessel opening must be removed before the closure 2 can be placed over the exterior of the blood vessel to seal the opening. The closure 1 is positioned near the open end of the sheath 10 before or after the sheath has been removed from the opening. After the sheath 10 has been removed from the puncture 20, the closure 2 may be placed over the opening. Immediately after that placement, the sheet 2 is pushed against the puncture 20 so that a multiplicity of barbs 4 penetrate the exterior 23 of the blood vessel 21 to seat the closure. Then, pusher rod 6 is released from sheet 2 and removed from the site. Sheath 10 through which the pusher rod 6 had extended can be removed an the same time.

I prefer to make the sheet 2 of a flexible material so that it not only can and will conform to the wall of blood vessel 21, but also can be fitted and moved within sheath 10. As illustrated in FIG. 7, one may wish to roll the sheet about the pusher rod 6 to fit it through the sheath 10. Alternatively, the sheet may be flexible enough to allow it to curl somewhat as it passes through the sheath. That way the sheet 2 can be larger in all dimensions than the diameter of the sheath 10.

I prefer to localize the area around the puncture site before applying the closure 1. As shown in FIG. 8, this can be done through the use of an ultrasonic transducer 24 which is inserted through sheath 10 using rod 26. When the transducer 24 is adjacent the puncture site, ultrasound transmissions are begun to localize the area around the puncture site.

I also prefer to coat the barbs on my closure with collagen. That coating will promote thrombogenesis at the puncture site. By using a collagen coated closure I am able to reduce the post-procedure bleeding time from thirty to forty minutes in the conventional post-angioplasty patient to a five minute post procedure bleeding time.

Many patients who undergo angioplasty procedures frequently are receiving heparin which acts as a blood thinner and inhibits clotting. In some instances the use of heparin is discontinued or reversed to promote clotting following angioplasty. However, doctors are often reluctant to reverse heparin in a recently dialated blood vessel. Use of the present closure will allow removal of the sheath without heparin reversal.

Since the sheet 2 and barbs 4 remain in the body they must be made from a biocompatible material which has sufficient flexibility for insertion into the blood vessel. One suitable material is silicon. Some plastics of the type used for other types of implantable structures may also be appropriate.

I anticipate that for most applications sheet 2 will be between 0.5 and 1.5 centimeters in length and have a thickness of 0.3 $\mu$m. The barbs preferably will have a height of 50 to 100 $\mu$m or greater. They must be of a configuration capable of piercing the blood vessel wall and remain anchored therein. In the drawings I have shown one preferred configuration, but other types of barbs may also prove suitable.

Although I have described and shown certain present preferred embodiments of my closure and method of inserting same, it should be distinctly understood that the invention is not limited thereto, but may be variously embodied within the scope of the following claims.

I claim:

1. A closure for sealing a puncture in a blood vessel comprising:
   a) a sheet adapted to conform to a blood vessel wall, the sheet having a top surface and a bottom surface, one of the top surface and the bottom surface having
   a plurality of barbs covering, distributed and interspersed throughout, the barbs being sufficient in number, and being positioned and configured so that a multiplicity of barbs will pierce and anchor in the blood vessel wall; and
   b) a pusher rod having means for releasable attachment to the sheet and being releasably attached to the sheet, the pusher rod for pushing the sheet through the puncture, anchoring the sheet to cover and seal the puncture and seat the barbs into the blood vessel wall and thereafter releasing from the sheet.

2. The closure of claim 1 wherein the sheet is capable of being rolled around the pusher rod to a generally cylindrical shape having a diameter smaller than a diameter of the puncture for insertion through the puncture into the blood vessel where the sheet is unrolled to engage an inner wall of the blood vessel.

3. The closure of claim 1 wherein the barbs extend 50 $\mu$m to 100 $\mu$m from one of the top surface and the bottom surface of the sheet.

4. The closure of claim 1 wherein the barbs are coated with collagen.

5. The closure of claim 1 also comprising a sheath into which the sheet with barbs and at least a portion of the pusher rod are fitted.

6. A method of closing a puncture in a blood vessel comprising the steps of:
   a) providing a closure comprised of
      i) a sheet adapted to conform to a blood vessel wall, the sheet having a top surface and a plurality of barbs covering, distributed, and interspersed throughout the top surface, the barbs being sufficient in number, and being positioned and configured so that a multiplicity of barbs will pierce and anchor in the blood vessel wall; and
      ii) a pusher rod releasably attached to the top surface of the sheet;
   b) inserting a sheath through the puncture;
   c) rolling the sheet around the pusher rod to a cylindrical shape of a diameter smaller than a diameter of the puncture;
   d) pushing the closure through the sheath into the blood vessel;
   e) unrolling the sheet;
   f) anchoring the sheet to cover and seal the puncture and seat the multiplicity of barbs into the blood vessel wall
   g) releasing the pusher rod from the sheet; and
   h) removing the sheath and the pusher rod.

7. The method of claim 6 wherein the barbs extend 50 $\mu$m to 100 $\mu$m from the top surface of the sheet.

8. The method of claim 6 wherein the barbs are coated with collagen.

9. The method of claim 6 also comprising the step of localizing a portion of the blood vessel adjacent the puncture by injecting an ultrasound transducer through the sheath after step a) and before step b).

10. The method of claim 6 wherein the sheet is anchored to an interior surface of the blood vessel.

11. A method of closing a puncture in a blood vessel wherein a sheet is anchored to an exterior surface of the blood vessel comprising the steps of:
   a) positioning an open end of a sheath near and outside the puncture;
   b) releasably attaching a pusher rod to a sheet adapted to conform to an exterior surface of a blood vessel, the sheet having a top surface, a bottom surface and a plurality of barbs covering, distributed and interspersed throughout the bottom surface of the sheet, the barbs being sufficient in number, and being positioned and configured so that a multiplicity of barbs will pierce and anchor in the exterior surface of the blood vessel;
   c) rolling the sheet around the pusher rod;
   d) pushing the sheet through the sheath;
   e) positioning the sheet over the puncture;
   f) unrolling the sheet;
   g) anchoring the sheet on the exterior surface of the blood vessel to cover and seal the puncture and seat the multiplicity of barbs into the blood vessel wall;
   h) releasing the pusher rod from the sheet; and
   i) removing the sheath and the pusher rod.

12. The method of claim 11 wherein the barbs extend 50 $\mu$m to 100 $\mu$m from the bottom surface of the sheet.

13. The method of claim 11 wherein the barbs are coated with collagen.

* * * * *